United States Patent [19]

Willard

[11] Patent Number: 5,423,838
[45] Date of Patent: Jun. 13, 1995

[54] ATHERECTOMY CATHETER AND RELATED COMPONENTS

[75] Inventor: Lloyd K. Willard, Miltona, Minn.

[73] Assignee: SciMed Life Systems, Inc., Maple Grove, Minn.

[21] Appl. No.: 82,931

[22] Filed: Jun. 25, 1993

Related U.S. Application Data

[63] Continuation of Ser. No. 765,174, Sep. 25, 1991, abandoned, which is a continuation of Ser. No. 435,280, Nov. 13, 1989, Pat. No. 5,085,662.

[51] Int. Cl.⁶ ............................................. A61B 17/22
[52] U.S. Cl. .................... 606/159; 606/169; 606/194; 128/660.03
[58] Field of Search .............. 606/159, 169, 170, 171, 606/194; 604/22, 96, 53; 128/660.03

[56] References Cited

U.S. PATENT DOCUMENTS

| | | |
|---|---|---|
| 2,714,890 | 8/1955 | Vang . |
| 3,352,303 | 11/1967 | Delaney . |
| 3,565,062 | 2/1971 | Kuris . |
| 3,730,185 | 5/1973 | Cook et al. . |
| 3,776,238 | 12/1973 | Peyman et al. . |
| 3,811,446 | 5/1974 | Lerwick et al. . |
| 3,832,776 | 9/1974 | Sawyer . |
| 4,217,904 | 8/1980 | Zahorsky . |
| 4,315,511 | 2/1982 | Chin . |
| 4,431,006 | 2/1984 | Trimmer et al. . |
| 4,445,509 | 5/1984 | Auth . |
| 4,474,180 | 10/1984 | Angulo . |
| 4,582,181 | 4/1986 | Samson . |
| 4,669,469 | 6/1987 | Gifford, III et al. . |
| 4,679,557 | 7/1987 | Opie et al. . |
| 4,685,458 | 8/1987 | Leckrone . |
| 4,735,606 | 4/1988 | Davison . |
| 4,747,821 | 5/1988 | Kensey et al. . |
| 4,748,982 | 6/1988 | Horzewski et al. . |
| 4,762,129 | 8/1988 | Bonzel . |
| 4,765,332 | 8/1988 | Fischell et al. . |
| 4,772,268 | 9/1988 | Bates . |
| 4,781,186 | 11/1988 | Simpson et al. . |
| 4,794,931 | 1/1989 | Yock . |
| 4,819,635 | 4/1989 | Shapiro . |
| 4,842,582 | 1/1989 | Mahurkar . |
| 4,846,192 | 7/1989 | McDonald . |
| 4,854,325 | 8/1989 | Stevens . |
| 4,920,954 | 5/1990 | Alliger et al. . |
| 4,936,845 | 6/1990 | Stevens . |
| 4,940,468 | 7/1990 | Petillo . |
| 4,950,277 | 8/1990 | Farr . |
| 4,961,809 | 10/1990 | Martin . |
| 4,979,951 | 12/1990 | Simpson ............................. 606/159 |
| 5,024,234 | 6/1991 | Leary et al. . |
| 5,054,492 | 10/1991 | Scribner et al. . |
| 5,163,433 | 11/1992 | Kagawa et al. . |
| 5,203,338 | 4/1993 | Jang . |
| 5,350,395 | 9/1994 | Yock ..................................... 604/96 |

FOREIGN PATENT DOCUMENTS

2929562A1 1/1980 Germany .

OTHER PUBLICATIONS

"Balloon Catheters For Percutaneous Insertion Into The Vascular System", by Bjorn Nordenstrom, Dept. of Diagnostic Roentgenology, Mar. 2, 1962.

*Primary Examiner*—Michael H. Thaler
*Attorney, Agent, or Firm*—Nawrocki, Rooney & Sivertson

[57] ABSTRACT

An atherectomy catheter includes a catheter shaft having three lumens. The central lumen supports a central wire on which is mounted a shell-shaped cutter. The cutter is exposed to the exterior of the shaft via a cutting window, and the cutter is mounted in a housing integral with the catheter shaft. An upper lumen receives material severed by the cutter as severed material is pushed proximally by the cutter during a cutting stroke. The lower lumen is used to inflate a balloon situated opposite the cutting window. The cutter is arranged to cut when pulled proximally, and is oscillated through a short stroke while the user moves the cutter across the cutting window. A guide wire extends laterally outside of the catheter shaft to a point past the cutter, where it enters the central lumen distally of the central wire.

17 Claims, 5 Drawing Sheets

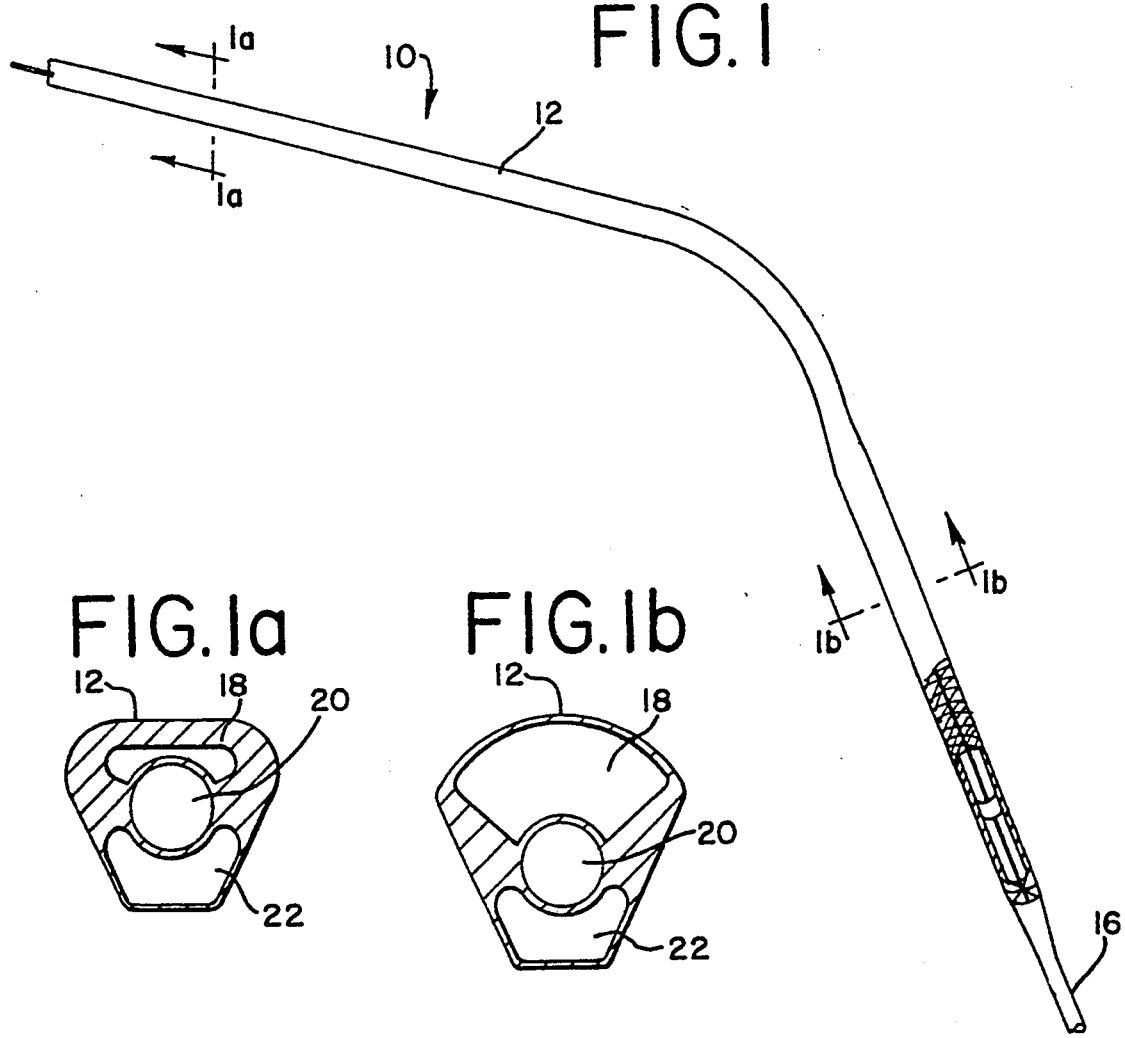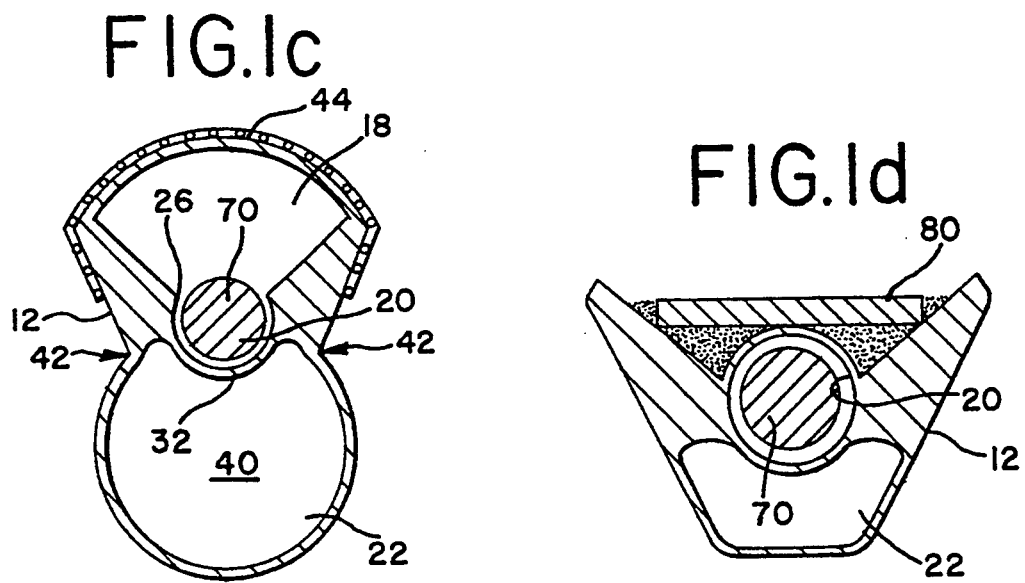

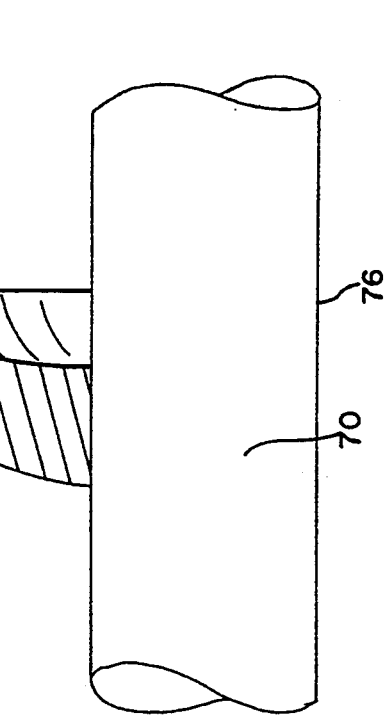
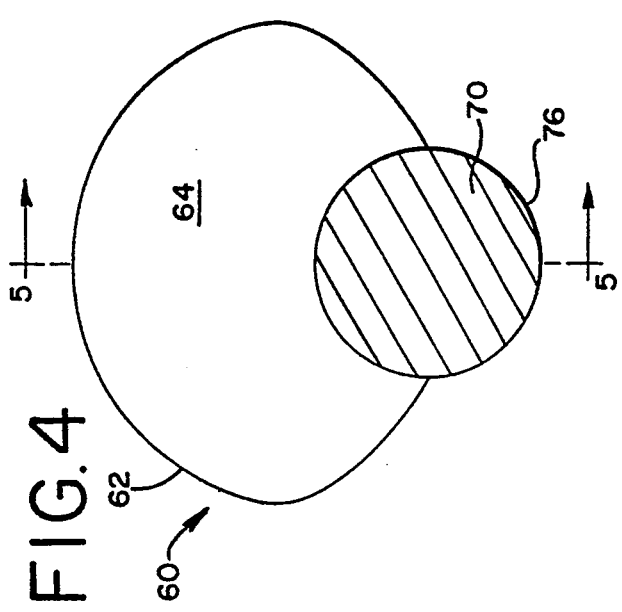
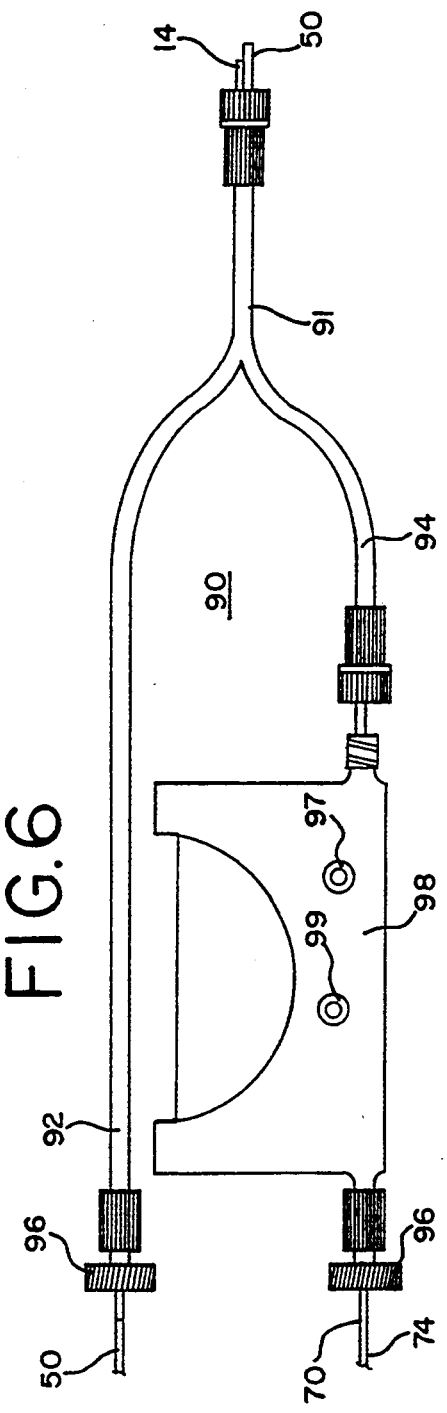

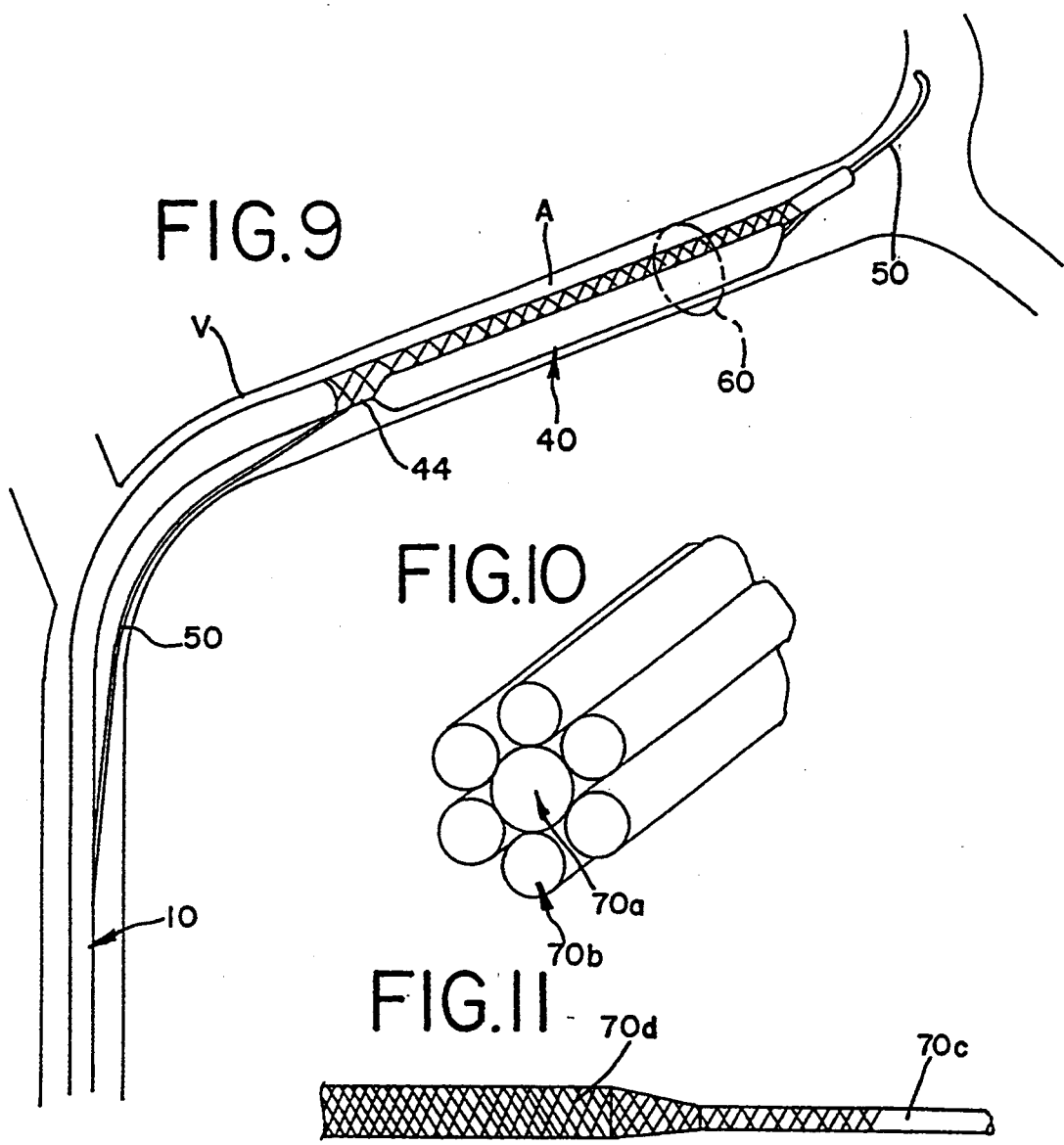

ATHERECTOMY CATHETER AND RELATED COMPONENTS

REFERENCE TO RELATED APPLICATIONS

This application is a continuation of Ser. No. 07/765,174 filed Sep. 25, 1991, now abandoned, which was a continuation of Ser. No. 07/435,280 filed Nov. 13, 1989, now U.S. Pat. No. 5,085,662.

BACKGROUND OF THE INVENTION

This invention relates to an improved atherectomy catheter for severing and removing atheroma, calcific deposits, thrombus and related materials from blood vessel walls, and to components for such catheters. As will be apparent from the following discussion, certain of these components can be used in other types of catheters.

Atherectomy catheters have been proposed for removing material from an atheroma in the vascular system. Gifford U.S. Pat. No. 4,669,469 and Simpson U.S. Pat. No. 4,781,186 disclose two such devices, both of which have a distal end that defines an opening on one side and an inflatable balloon on the other. A rotary cutter is mounted within the distal end to be advanced distally while being rotated so as to cut through material that has been pushed into the opening by the inflated balloon opposite the opening. The device illustrated in the Gifford patent utilizes a guidewire that extends axially through a tube used to rotate and advance the rotary cutter.

Fischell U.S. Pat. No. 4,765,332 discloses an atherectomy catheter that includes a distal tubular blade that cuts as it is pulled proximally. During the actual cutting, the entire blade is exposed around the perimeter of the device.

Another approach is described in Leckrone U.S. Pat. No. 4,685,458, which utilizes a catheter having three lumens. The first lumen receives removed material, the second receives a guidewire, and the third lumen is used to inflate a balloon opposite the material-receiving region of the distal end of the catheter. The disclosed catheter uses laser energy, a heated element or a fixed knife to remove material.

Auth U.S. Pat. No. 4,445,509 discloses a method and apparatus for removing vascular deposits having a rotary cutting tool that defines spirally-shaped cutting flutes shaped to remove relatively more rigid deposits without harming relatively more elastic vascular walls. The disclosed cutter is said to operate preferentially against relatively hard material such as calcific plaque without cutting relatively soft material such as the vessel.

A somewhat similar approach is used in Kensey U.S. Pat. No. 4,747,821 which utilizes a rotary impacting head that is shaped not to harm the visco-elastic vessel wall. However, when the impacting head contacts atherosclerotic tissue, the increased hardness of the tissue is said to render it susceptible to disruption by the impacting head.

Shapiro U.S. Pat. No. 4,819,635 discloses a tubular microsurgery cutting apparatus intended for use in opthamic surgery. This apparatus includes an outer tube that defines a side opening at a distal end through which material to be severed passes. A tubular cutter is mounted within the outer tube and is axially oscillated by a pneumatic system such that the oscillation causes the cutter to move across the entire opening with each stroke. This system appears to contemplate the use of a relatively long stroke, and no means are provided for shifting the center of oscillation of the cutting element along the length of the opening in the outer tube.

It is an object of the present invention to provide an improved atherectomy catheter which is well-suited to the removal of atheroma, calcific deposits and thrombus without damaging the vessel wall, which uses a cutting stroke that is oriented proximally, which captures and removes a large quantity of removed material without requiring the catheter to be removed from the vessel, which utilizes a remarkably flexible housing for the cutter element that facilitates placement of the catheter in small and tortuous vessels, which combines axial oscillation of the cutter element with movement of the center of oscillation along the cutting window to provide improved control and cutting action, and which can be guided to the treatment site by a guidewire which does not occupy volume within the body of the catheter shaft proximally of the cutter element.

SUMMARY OF THE INVENTION

The atherectomy catheter disclosed below includes a number of important features that cooperate together to achieve surprisingly effective operation. It should be understood, however, that these features are not required to be used in combination with one another, but can also be used independently in appropriate applications.

According to a first feature of this invention, an atherectomy catheter of the type comprising a catheter shaft having a proximal end portion and a distal end portion, and a laterally facing cutting window located in the distal end portion is provided with a cutter element mounted in the distal end portion for axial motion and alignable with the cutting window. This cutting element defines a sharpened cutting edge oriented to cut material which has passed through the cutting window as the cutter element is moved axially towards the proximal end portion. With this arrangement the cutter element pushes removed material proximally during the cutting stroke, and in this way assists in the collection of the severed material in the catheter proximally of the cutter element. A relatively large volume of severed material can be collected in this way without removing or emptying the catheter.

According to a second feature of this invention, a catheter of the type described above is provided with a cutter element mounted in the distal end portion for axial motion and alignable with the cutting window. This cutter element defines a sharpened cutting edge oriented to cut as the cutter element moves axially. A motion transmitting member supports the cutter element and means are provided for oscillating the motion transmitting element axially to oscillate the cutter element. The cutting window defines a length, the oscillating means oscillates the motion transmitting member through an axial stroke, and the stroke is less than the length. Additionally, the oscillating means is axially movable with respect to the catheter shaft to allow a user to move the motion transmitting member axially to pull the catheter element along the cutting window independently of oscillatory motion of the cutter element. Such axial oscillation can be adjusted to optimize cutting of the cutter element against relatively harder atheromas, calcific deposits, and the like while minimizing damage to the visco-elastic native vessel. By combining such oscillation with movement of the cutter axially in a manner independent of the oscillation, two distinct types of cutting motions are provided which allow considerable flexibility and control to the clinician.

According to a third feature of this invention, a catheter is provided for use with a guidewire and the catheter includes means for coupling the guidewire to the distal portion of the catheter shaft while allowing axial movement therebetween. The guidewire extends laterally outside and alongside the catheter shaft proximally of the coupling means. This arrangement allows a single lumen in the catheter to serve two distinct functions. Distally, the lumen can be used as the coupling means to couple the guidewire to the catheter. Because the guidewire exits the lumen at a point at the distal end of the catheter shaft, the remaining proximally disposed portion of the lumen can be used for other functions, such as to carry the motion transmitting member described above. This aspect of the invention is not limited to use with an atherectomy catheter, but can also be used with other types of treatment and sensing catheters where there is a need to conduct an elongated member such as sensor leads or to provide a lumen such as a balloon inflating lumen in the proximal portion of the catheter shaft.

According to a fourth aspect of the invention, an atherectomy catheter of the type described above is provided with a cutter element mounted in the distal end portion for axial motion and alignable with the cutting window. This cutter element defines a sharpened cutting edge oriented to cut as the cutter element moves axially, and the distal end portion of the catheter shaft is flexible and is formed of an elastomeric material secured to the catheter shaft such that the distal end portion is configured to be advanced through a tortuous blood vessel. This enhances the flexibility and the maneuverability of the distal end of the catheter.

According to a fifth aspect of this invention the cutter element for one of the atherectomy catheters described above is fixed to a motion transmitting member and is shaped to extend asymmetrically from one side of the motion transmitting member toward the cutting window. The cutter element defines a smoothly curved concave surface adjacent to the cutting edge, which is shaped to redirect materials severed by the cutting edge toward a direction of motion defined by the cutter element. The preferred cutter element is shell shaped, and its smoothly curved concave surface is shaped to redirect the severed material into the catheter shaft itself proximally of the cutter element. Because the cutter extends asymmetrically from one side of the motion transmitting member, the opposite side of the motion transmitting member can be firmly supported by the catheter shaft in order to improve the stability and controllability of the cutting action.

The invention itself, together with further objects and attendant advantages, will best be understood by reference to the following detailed description, taken in conjunction with the accompanying drawings.

BRIEF DESCRIPTION OF THE DRAWINGS

FIG. 1 is a side view of a distal portion of an atherectomy catheter which incorporates a presently preferred embodiment of this invention.

FIGS. 1a, 1b, 1c and 1d are cross-sectional views taken along corresponding section lines of FIGS. 1 (1a and 1b) and 2 (1c and 1d).

FIG. 4 is a partial sectional view taken along line 4—4 of FIG. 2.

FIG. 5 is a partial sectional view taken along line 5—5 of FIG. 4.

FIG. 6 is a side view of a manifold system coupled to the proximal end of the catheter FIG. 1.

FIG. 9 is a schematic view of the distal end of the catheter FIG. 1 in use.

FIGS. 10 and 11 are fragmentary perspective views of portions of two suitable motion transmitting members for the catheter of FIG. 1.

FIGS. 12a and 12b are schematic sectional views of portions of two additional motion transmitting members for the catheter of FIG. 1.

DETAILED DESCRIPTION OF THE PRESENTLY PREFERRED EMBODIMENTS

Figure 2:
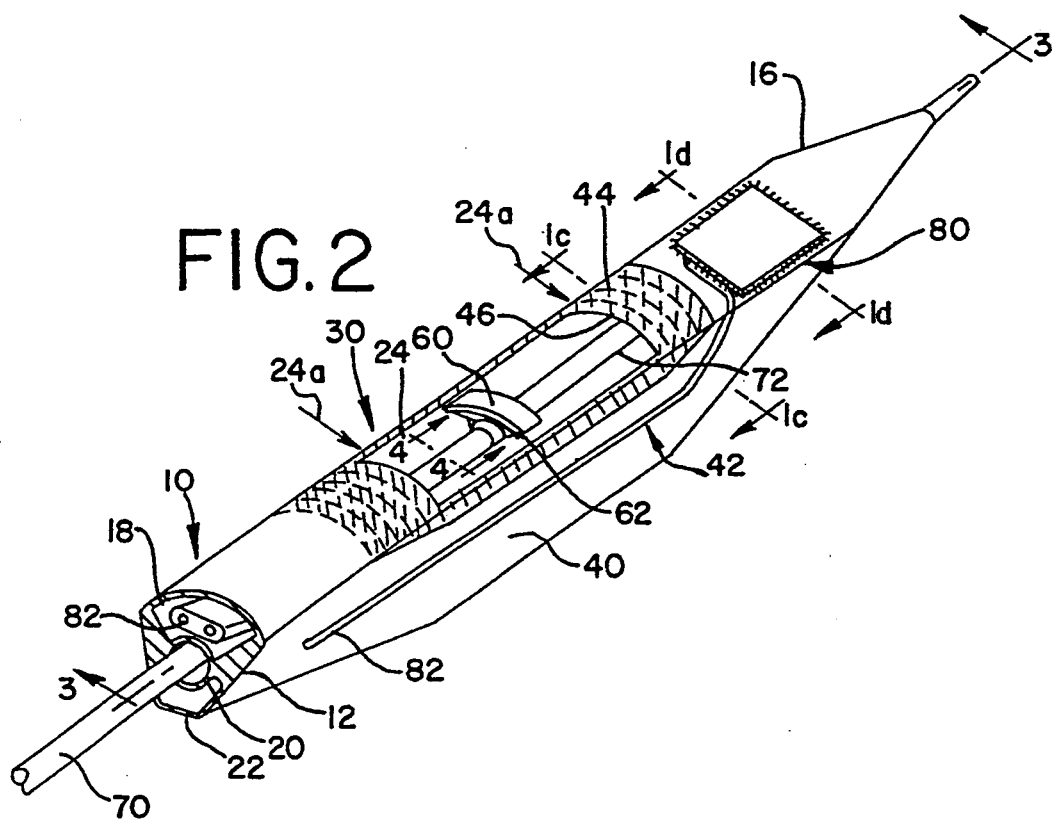
FIG. 2 is a perspective view of the distal portion of the catheter of FIG. 1.

Turning now to the drawings, FIG. 1 shows a side view of a distal portion of a catheter 10 which incorporates the presently preferred embodiment of this invention. The catheter 10 includes an extruded elastomeric shaft 12 which defines a distal end 16 and a proximal end 14 (FIG. 6).

The cross sectional views of FIGS. 1a–1d show sections through the shaft 12 at four points. FIG. 1b shows the cross sectional shape of the shaft 12 as extruded. The shaft 12 include an upper lumen 18, a central lumen 20 and a lower lumen 22. Through the majority of the proximal portion of the shaft 12 the shaft 12 is reformed with heat to the reduced cross sectional size shown in FIG. 1a.

As described below, the distal end portion of the shaft 12 defines a housing for a cutter element as well as a balloon 40, FIG. 1c shows a cross sectional view through the balloon 40 and in this region the shaft 12 has been reformed with heat to expand the lower lumen 22 to form the balloon 40. For example, a suitable reforming operation involves placing a cooled wire in the central lumen 20, enclosing the distal end portion in a suitable mold, and then heating the material of the shaft 12 with a heated fluid while expanding the lower lumen 22 to the shape shown in FIG. 1c by applying pressure to the lumen.

FIG. 2 shows a perspective view of the distal end portion 16 of the catheter 10. As shown in FIG. 2 the lower lumen 22 expands gradually to form the balloon 40. Thus, the balloon 40 is a one piece, integral portion of the shaft 12 and is formed of the same elastomeric material. As shown in FIG. 2 a portion of the upper lumen is cut away to form a cutting window 24 which is generally rectangular in shape. In addition, the upper portion of the upper lumen is cut away in the region of a piezo-electric crystal 80 which forms an imaging sensor. FIG. 1d is a cross sectional view through the sensor 80, which is adhesively mounted in place above the central lumen 20. The sensor 80 is not required in many applications, in which case it may simply be deleted.

Figure 3:
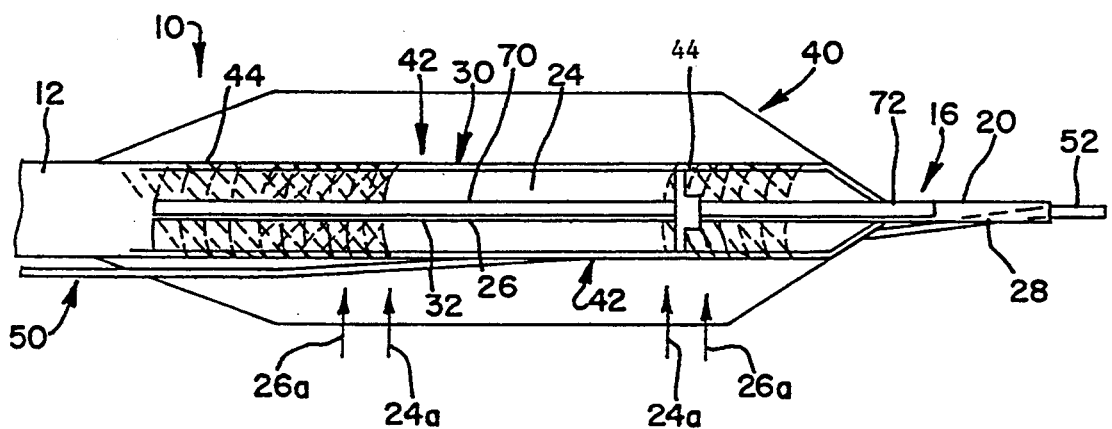
FIG. 3 is a sectional view taken along line 3—3 of FIG. 2.

A portion of the central lumen 20 is removed to form a lumen window 26 aligned with the cutting window 24 and extending slightly beyond the cutting window 24 in both the proximal and distal axial directions. In FIG. 3 the axial extent of the cutting window 24 is denoted by arrows 24a, and the axial extent of the lumen window 26 is denoted by arrows 26a. In effect, the upper lumen opens out to one side of the catheter 10 opposite the balloon 40 in the region of the cutting window 24, and the central lumen 20 similarly opens out in the region aligned with the cutting window 24. The central lumen 20 extends axially completely to the distal end 16, and a passageway 28 is formed in a side wall of the central lumen 20 distally of the balloon 40, as shown in FIG. 3.

The cutting window 24 is reinforced by a flexible reinforcing element 44 such as a metal braid which is adhesively secured to the shaft 12 by an epoxy adhesive, as shown in FIG. 1c. This reinforcing element 44 serves two purposes. It reinforces the catheter shaft 12 in the region of the cutter to prevent the cutter from inadvertently leaving the shaft and damaging the adjacent artery, and it retains the catheter shaft 12 in its originally extruded shape when cutting forces are applied. The reinforcing element 44 defines an opening 46 aligned with and defining the cutting window 24.

As shown in FIGS. 2, 4, and 5, the catheter 10 includes a cutter element 60 which defines a cutting edge 62 and a proximally oriented face 64. The proximally oriented face 64 is smooth and concave, and is shaped to redirect severed material proximally, into the upper lumen 18.

The cutter element 60 is bonded (as for example by brazing) to a motion transmitting member or central wire 70 which defines a distal end 72 that is supported and completely captured in the central lumen 20 (FIG. 3) and a proximal end 74 (FIG. 6). As best shown in FIG. 5, the central wire 70 defines a surface 76 opposite the cutter element 60 which is unobstructed by the cutter element 60.

As shown in FIGS. 2 and 3 the central wire 70 is disposed in the central lumen 20 for axial movement. The remaining portion of lower lumen 22 opposite the cutter element 60 forms a cutter element support surface 32 which supports the cutter element 60 against lateral movement towards the balloon 40.

From this description it should be apparent that the distal end 16 of the shaft 12 forms a housing 30 for the cutter element 60. This housing 30 is flexible and is configured to be advanced through a tortuous blood vessel in use. The housing 30 itself is formed of an elastomeric material and is integral with the shaft 12.

The catheter 10 is intended to be navigated to the treatment site by a guidewire 50 which defines a distal end 52. Throughout the large majority of the length of the catheter 10, the guidewire 50 passes alongside and outside of the catheter 10. Distally of the balloon 40, the distal end 52 of the guidewire 50 passes through the passageway 28 into the central lumen 20 and out of the central lumen 20 distally of the catheter 10. The guidewire 50 passes alongside the balloon 40 in a channel or groove 42 formed between the balloon 40 and the reinforcing element 44.

In a somewhat similar manner the sensor 80 is interconnected with proximally located electronic circuitry (not shown) by leads 82 which pass alongside the balloon 40 in one of the channels or grooves 42. The leads 82 pass into the upper lumen 18 through a puncture in the upper lumen 18 proximally of the balloon 40, as shown in FIG. 2. The leads 82 are typically adhesively secured to the exterior of the catheter 10 in one of the channels or grooves 42. The puncture used to pass the leads 82 into the upper lumen 16 can be formed approximately four centimeters proximally of the balloon 40. Such punctures can then be sealed with a suitable adhesive.

FIG. 6 shows a manifold system 90 adapted for connection to the proximal end 14 of the catheter shaft 12 and the guidewire 50. This manifold system 90 includes a divider tube 91 having first and second branches 92, 94. The guidewire 50 and the catheter shaft 12 enter the divider tube 91 in side-by-side orientation. The proximal end of the guidewire 50 exits from the first branch 92 while the proximal end of the central wire 70 exits from the second branch 94. Hemostasis valves 96 are provided to allow axial movement of both the guidewire 50 and the central wire 70. The upper and lower lumens 18, 22 are in fluid communication with a port assembly 98 that includes a balloon inflation port 99 adapted to receive fluid to inflate the balloon 40 via the lower lumen 22, and a vacuum port 97 interconnected with the upper lumen 18. Fluid can be drawn out of the vacuum port 97 to assist in the removal of severed material through the upper lumen 18.

Figure 7:
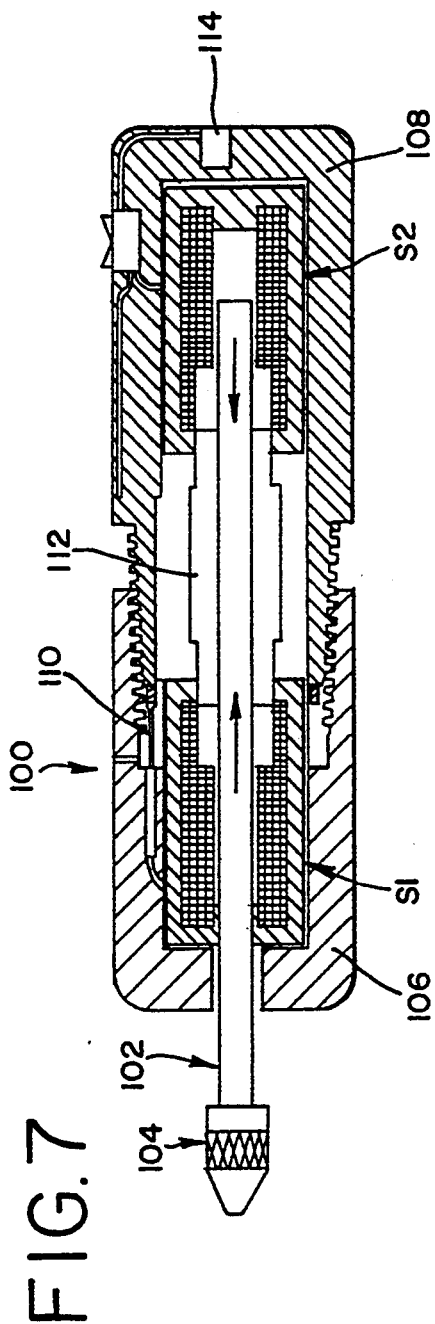
FIG. 7 is a sectional view of an oscillating driver for the catheter FIG. 1.

FIG. 7 shows an oscillating means 100 that can be coupled to the proximal end of the central wire 70. The oscillating means 100 includes a low mass magnetic plunger 102 which terminates at one end with a wire chuck 104 adapted to secure the central wire 70. The oscillating means 100 includes two push-type solenoids S1, S2 which are mounted at opposite ends of a housing 106, 108. The two portions of the housing 106, 108 are threadedly interconnected, and a brush system 110 transmits electrical power from the housing 106 to the housing 108 while allowing axial movement between the two. A stop block 112 is mounted to the plunger 102 within the housing 106 between the two solenoids S1, S2. Power for the solenoids S1, S2 is introduced via a power connector 116 and is transmitted to the solenoid S1 via the brush system 110.

Figure 8:
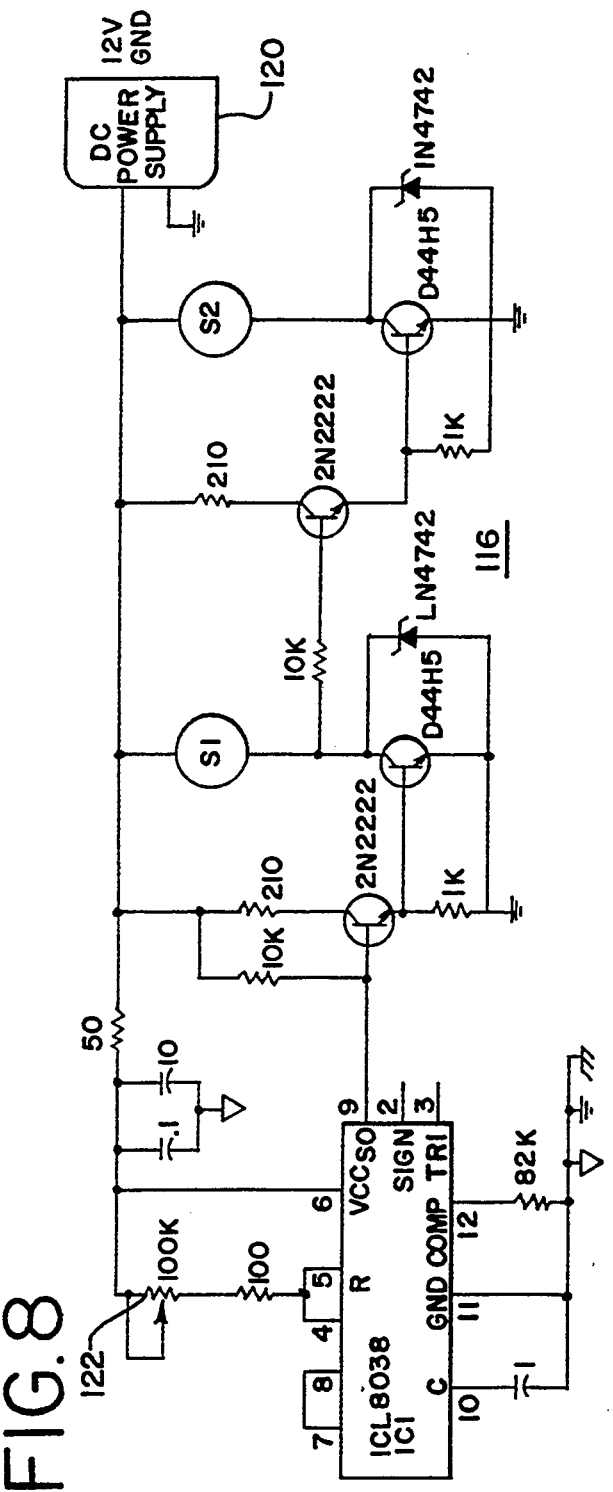
FIG. 8 is an electrical schematic diagram of a driver circuit for the driver FIG. 7.

FIG. 8 shows a schematic diagram for a suitable solenoid driver circuit 118 which is powered by a variable DC voltage supplied by a DC power supply 120. A frequency adjusting potentiometer 122 operates to vary the frequency of oscillation.

When powered by the driver circuit 116, the oscillating means 100 energizes the solenoids S1, S2 alternatively in a cyclical manner and at a frequency determined by the potentiometer 122. The clinician can adjust the stroke of oscillation by turning the housing 106 relative to the housing 108 to modify the axial separation between the two solenoids S1, S2. The clinician can adjust the frequency of oscillation with the potentiometer 122 and the power of oscillation by adjusting the voltage supplied by the power supply 120. It is anticipated that a preferred stroke will be less than 0.05 inch and most preferably less than 0.03 inch.

It should be noted that the oscillating means 100 is mounted only to the central wire 70, and not to the manifold system 90. This allows the clinician to move the oscillating means 100 axially with respect to the manifold system 90 and thereby to move the cutter element 60 axially along the length of the cutting window 24. The cutter element 60 is oriented with the cutting edge 62 facing the proximate direction. By pulling on the oscillating means 100, the clinician can pull the cutter element 60 across the cutting window 24, thereby severing material which has entered the cutting window 24. During such large scale axial movements, the oscillating means 100 can be used to oscillate the cutter element 60 with a relatively short stroke, typically much less than the axial length of the cutting window 24. This oscillation provides a differential cutting action which is relatively more effective against more rigid material such as atheroma, calcific deposits and thrombus and less effective against elastic materials such as the native vessel wall.

FIG. 9 shows a schematic view of the catheter 10 in use. In FIG. 9 the balloon 40 is shown inflated inside a vessel V adjacent to an atheroma A to be removed. In order to navigate the catheter to this position, the guidewire 50 is inserted into the vessel V past the atheroma A. Then the catheter 10 is pushed down the guidewire 50, with the balloon 40 deflated. When the catheter 10 reaches the appropriate position the balloon 40 is oriented to align the cutting window 24 with the atheroma A. At this point, the cutter element 60 is positioned distally of the cutting window 24. This is possible because the lumen window 26 is made somewhat longer than the cutting window 24. The balloon 40 is then inflated, thereby pressing a portion of the atheroma A through the cutting window 24.

Once the catheter 10 has been positioned as shown in FIG. 9, the clinician can energize the oscillating means 100 to oscillate the cutter element 60 with the desired stroke, frequency and power. The clinician then pulls the cutter element 60 proximally to sever material from the atheroma A. The oscillating movement of the cutter element 60 enhances its cutting action and reduces stresses on the vessel wall and the catheter housing 30. The proximal face 64 of the cutter element 60 is concavely shaped to redirect severed material proximally into the upper lumen 18. The upper lumen 18 is relatively large in cross-sectional area and extends over the length of the catheter 10. The catheter 10 therefore can receive a large volume of severed material without being removed from the body. Once the cutter element 60 has been moved past the proximal end of the cutting window 24, the catheter 10 can be repositioned and additional cuts made as deemed appropriate by the clinician. The sensor 80 may provide imaging information helpful in orienting the catheter 10 properly. The channels or grooves 42 prevent the catheter 10 from completely obstructing blood flow during treatment, thereby allowing tissue perfusion distally of the atheroma A, even during treatment.

The disclosed arrangement for the guidewire 50 provides the important advantage that the catheter 10 can be removed form the guidewire 50 while leaving the guidewire 50 in place, as for example when it is desired to replace the catheter 10 with an angioplasty catheter. This is done by holding the guidewire 50 in place distally of the manifold system 90 while withdrawing the catheter 10 and the manifold system 90. Once the catheter 10 is removed from the patient, it can be removed from the guidewire 50 and replaced with another catheter.

The following information is provided better to define the best mode of the invention, and is not intended to be limiting.

The cutter element 60 should be formed of a material that is tough, high in ultimate strength and corrosion resistant. Both stainless steels and tool steels can be used. At present, tool steels type D2 and A2 are considered most preferable. These metals provide high toughness, and can be made suitably corrosion resistant by ion sputtering with nitrogen. Ion implantation may also be used to enhance both corrosion resistance and toughness. Other steels that offer similar characteristics are A9, CPM, M2, M4, T4 and T5. In general, the cutter element 60 may be hardened using ion implantation, carburization, carbonitriding, and nitrocarburization techniques. Alloys of cobalt, titanium, tungsten and others may be used. Stainless steels can be selected from AISI types 301, 302, 304 and 314, for example. Additionally, super alloys such as a A286, 14-9DL and D979 as well as other materials may be suitable for selected applications.

The catheter shaft 12 can be extruded from a polyolifin copolymer (such as that sold by DuPont under the tradename SURLYN as Resin No. 8527) using secondary treatment with 5 to 50 Mega-rad electron beam irradiation to enhance strength in the region of the balloon 40. The divider tube 91 can be formed of any suitable material such as polyethylene, polyolifin, polyurethane or nylon.

The oscillator means 100 can be varied in frequency between 0 and 500 Hertz. It is anticipated that in many applications the preferred operating range will be 20 to 200 Hertz.

The amplitude of oscillation or stroke of the oscillating means 100 can be adjusted from 0 (oscillating means off for totally manual cutting) to 0.25 inches. The preferred amplitude will vary with the application and the preferences of the clinician. It is anticipated that the amplitude of oscillation will typically be less than 0.05 inches and most generally in the range of 0.01 to 0.03 inches.

The flexible reinforcing element 44 can be formed of a stainless steel mesh. This mesh can be formed of either flat wound wire of approximately 0.002 by 0.005 inches or round wire of about 0.0025 inches to 0.0030 inches in diameter. The reinforcing element 44 may also be made of round fiber material such as polyaramid. The braid pattern is designed to cover 60 to 80% of the shielded area. The edges of the reinforcing element 44 are sealed with solder or adhesive, and the dimensions of the cutting window 24 can vary from between about 0.025 inches to 0.040 inches in width and 0.080 inches to 0.160 inches in length.

A number of approaches can be used to form the central wire 70. For example, the wire 70 can be made up of a core wire 70a which is surrounded by a set of axially extending perimeter wires 70b secured, for example, by brazing to the core wire (FIG. 10). The central core wire 70a can be made of a relatively high tensile/compression material while the perimeter wires 70b which encapsulate the core wire 70a are smaller and optionally formed of materials with lower ultimate tensile strength and greater flexibility. Silver-tin solder can be used to join the core wire 70a to the perimeter wires 70b. Table I shows alternate arrangements for this type of core wire 70.

TABLE 1

| Diameter of Wire 70 | | Core Wire 70a | | | Perimeter Wire 70b | | |
|---|---|---|---|---|---|---|---|
| | | Dia. (in.) | Mat'l | Tensile (KSI) | Dia. (in.) | Mat'l | Tensile (KSI) |
| .014 | * | .008 | 304SS | 300 min | .003 | 304SS | 200–300 |
| .016 | * | .008 | 304SS | 300–440 | .004 | 304SS | 200–300 |
| | | .010 | 304SS | 240–330 | .003 | 304SS | 200–300 |
| .018 | * | .008 | 304SS | 300–440 | .005 | 304SS | 150–220 |
| | | .010 | 304SS | 260–330 | .004 | 304SS | 150–220 |

* Denotes preferred configuration

Another approach to the formation of the central wire 70 is to provide a central core wire 70c approximately 0.010 inches in diameter which tapers to a distal end of 0.005 to 0.008 inches in diameter. This core wire 70c is encapsulated by a 12 to 16 wire braid 70d of 0.002 to 0.003 inch diameter stainless steel wire. The pitch of the braid may be varied from 12 to 30 picks per inch to vary stiffness. The central core wire 70c is formed of high tensile stainless steel wire. The preferred embodiment uses a 0.008 inch minimum diameter core wire 70c with a 16 wire braid 70d. The central core wire is 304 stainless steel with a tensile strength of 400 Ksi minimum. The braiding wire is 0.002 inch diameter with a tensile strength of 740 Ksi minimum. The pick density may be varied from 12 to 30 picks per inch without significantly affecting the mechanical characteristics. The presently preferred configuration uses 18 to 26 picks to inch. Wires are stranded in four groups of four and are affixed by soldering to the two ends of the core wire 70c. This approach provides for a reduction in cross-section at the distal end to increase flexibility.

A third approach for the wire 70 is to use a core wire 70e of the type described above which is wound in a linear fashion with a coiling wire 70f (FIGS. 12a, 12b). Either a single layer (FIG. 12a) or a double layer (FIG. 12b) of coiling wire 70f can be used. In the embodiment of FIG. 12b the two layers are wound in opposite directions. The wound coils are fixed both at the proximal and distal ends of the core wire by soldering or brazing 71. The braze or solder used in these embodiments is primarily silver braze (BAG-7) and BAR 560 (approximately 96 to 97.5% tin and 2.5 to 4.0% silver). In each case the cutter is affixed on top of the wire 70. Preferred wire and coil dimensions are indicated in Table 2 below (all dimensions in inches).

Of course, the embodiments described above can be modified to suit the intended application. For example, a mechanical oscillating means can be used in place of the electro-mechanical oscillating means described above. Alternately, a single voice coil type driver can be used in place of the pair of solenoids S1, S2 discussed above. Materials, dimensions, and geometry can all be varied widely.

TABLE 2

| Config. (FIG.) | Core Wire Dia. Prox. to Taper | Core Wire Dia. Distally of Taper | Coil Wire Dia. | Total Dia. (Proximal) | Total Dia. (Distal) |
|---|---|---|---|---|---|
| 12a | .012 | .006 | .002 | .016 | .010 |
| 12a | .012 | .006 | .0025 | .017 | .011 |
| *12a | .012 | .006 | .003 | .018 | .012 |
| 12b | .008 | .005 | .002 | .016 | .013 |
| *12b | .008 | .005 | .0025 | .018 | .015 |
| 12b | .008 | .005 | .003 | .020 | .017 |

*Denotes Preferred configurations.

I claim:

1. An intravascular imaging catheter assembly comprising:
    a catheter body having a proximal portion and a distal portion, the catheter body defining a drive shaft lumen and a guide wire lumen;
    a drive shaft located in said drive shaft lumen, the drive shaft axially movable within the drive shaft lumen;
    a piezoelectric transducer located in the distal portion proximate to a distal end of the drive shaft;
    at least one lead connected to the piezoelectric transducer and extending through to a proximal end of the catheter body;
    a channel for receiving a guide wire, the channel extending alongside the catheter for at least a portion thereof and disposed proximally of the guide wire lumen;
    a guide wire removably locatable in the catheter with a proximal portion of the guide wire locatable in the channel and a distal portion of the guide wire locatable in the guide wire lumen.

2. An intravascular catheter assembly comprising:
    a catheter body, a lumen extending through the catheter body, the lumen having a proximal portion, a distal portion and a distal lumen opening;
    an elongate member located in said lumen, said elongate member extending to the proximal portion of the catheter body;
    a channel for receiving a guide wire, the channel extending alongside the catheter for at least a portion thereof;
    a passageway between a distal end of the channel and the distal portion of the lumen; and
    a guide wire locatable in the catheter with a proximal portion of the guide wire located in the channel and a distal portion of the guide wire located in the distal portion of the lumen.

3. The invention of claim 2 in which said elongate member is a drive shaft.

4. An intravascular catheter assembly for treatment of occlusive diseases comprising:
    a catheter body having a lumen extending therethrough and a distal opening;
    a distal member for treating occlusive disease, the distal member operably to impart reciprocating oscillating movement;
    a drive shaft extending through the lumen and connected to the distal member;
    a connection member located at the proximal end of the drive shaft for imparting reciprocating oscillating movement to the drive shaft;
    a channel disposed proximally of the distal opening and extending alongside of a portion of the catheter; and a guide wire which can be slidably received in said catheter, such that said guide wire extends through the channel and the distal opening.

5. The invention of claim 4 further comprising:
    an actuating device located at a proximal portion of the drive shaft and adapted to operatively connect to the connection member to impart longitudinal movement to the proximal end of the drive shaft through the connection member, with the longitudinal movement conveyed to the distal member for treating occlusive device whereby the disease can be treated by the distal member.

6. The invention of claim 5 in which said actuating device is further adapted to impart oscillating longitudinal movement to the proximal portion of the drive shaft.

7. The invention of claim 5 in which said actuating device is adjustable to provide for varying the range of oscillating longitudinal movement of the drive shaft.

8. The invention of claim 5 in which said actuating device is adjustable to provide for varying the frequency of oscillation of the drive shaft.

9. The invention of claim 5 in which said actuating device includes means for imparting longitudinal movement with a frequency approximately between 0 and 500 hertz.

10. The invention of claim 5 in which said actuating device includes means for imparting longitudinal movement with a frequency approximately between 20 and 200 Hertz.

11. The invention of claim 5 in which said actuating device further comprises:

a driving circuit for generating an output; and a solenoid arrangement connected to the output of the driving circuit, said solenoid arrangement associated with the connection member at the proximal portion of the drive shaft and adapted to impart longitudinal movement to the proximal portion of the drive shaft in response to the driving circuit output.

12. The invention of claim 11 which said actuating device further comprises:

a housing for containing the solenoid arrangement;

a plunger having a first end and a second end, and first end connected to the proximal portion of the drive shaft through the connection member and said second end received in said housing in said solenoid arrangement.

13. The invention of claim 12 in which said housing is adjustable to enable varying the range of movement of the plunger second end and thereby the range of oscillating movement of the drive shaft.

14. The invention of claim 13 in which said solenoid arrangement comprises:

a first solenoid, and a second solenoid positioned distally of the first solenoid; and in which said plunger second end further comprises:

a stop block located approximately between the first solenoid and the second solenoid.

15. The invention of claim 11 in which said driving circuit output has a frequency and which said driving circuit comprises:

a frequency adjustment circuit to provide for varying the driving circuit output frequency.

16. The invention of claim 15 in which said frequency adjustment circuit further comprises a potentiometer.

17. The invention of claim 4 in which said device for treating the disease comprises:

a cutter element connected to the distal portion of the drive shaft.

* * * * *